United States Patent [19]

Grollier

[11] Patent Number: 4,961,754
[45] Date of Patent: Oct. 9, 1990

[54] ULTRAFINE INORGANIC POWDER CONTAINING MELANIN PIGMENTS, PROCESS FOR PREPARATION THEREOF AND ITS USE IN COSMETICS

[75] Inventor: Jean F. Grollier, Paris, France
[73] Assignee: L'Oreal, Paris, France
[21] Appl. No.: 220,264
[22] Filed: Jul. 18, 1988
[30] Foreign Application Priority Data
Jul. 17, 1987 [LU] Luxembourg .................. 86946
[51] Int. Cl.$^5$ .................. A61K 7/13; A61K 7/035
[52] U.S. Cl. .................. 8/423; 8/409; 424/69
[58] Field of Search .......... 424/406, 423, 424, 637, 424/649, 69; 548/469; 8/409

[56] References Cited

U.S. PATENT DOCUMENTS

| | | | |
|---|---|---|---|
| 3,194,734 | 7/1965 | Seemuller et al. | 548/469 |
| 4,776,857 | 10/1988 | Carroll et al. | 8/443 |
| 4,857,308 | 8/1989 | Fukasawa | 424/69 |

FOREIGN PATENT DOCUMENTS

| | | |
|---|---|---|
| 0030278 | 6/1981 | European Pat. Off. |
| 0220617 | 5/1987 | European Pat. Off. |
| 2044104 | 4/1971 | Fed. Rep. of Germany |
| 992700 | 10/1951 | France |
| 2154769 | 5/1973 | France |
| 2371917 | 6/1978 | France |
| 2401962 | 3/1979 | France |
| 2432035 | 2/1980 | France |

Primary Examiner—Paul Lieberman
Assistant Examiner—John F. McNally
Attorney, Agent, or Firm—Cushman, Darby & Cushman

[57] ABSTRACT

Powder consisting of inert inorganic particles having a particle size of less than 20 microns, containing on their surface a melanin pigment resulting from the oxidation of at least one indole dye of formula:

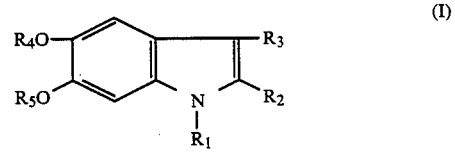

in which:

$R_1$ is hydrogen, alkyl or —$SiR_9R_{10}R_{11}$;

$R_2$ and $R_3$ denote hydrogen, alkyl, carboxyl, alkoxycarbonyl or —$COOSiR_9R_{10}R_{11}$; and $R_4$ and $R_5$ denote hydrogen, alkyl, formyl, acyl, alkenoyl, —$SiR_9R_{10}R_{11}$, —$P(O)(OR_6)_2$; or $R_6OSO_2$, or alternatively $R_4$ and $R_5$ together with the oxygen atoms form a ring;

$R_6$ and $R_7$ denoting hydrogen or alkyl, $R_8$ denoting alkoxy or mono- or dialkylamino, $R_9$ and $R_{10}$ and $R_{11}$ denoting alkyl.

11 Claims, No Drawings

ULTRAFINE INORGANIC POWDER CONTAINING MELANIN PIGMENTS, PROCESS FOR PREPARATION THEREOF AND ITS USE IN COSMETICS

The present invention relates to an inorganic powder containing melanin pigments, which is intended, in particular, to be used for dyeing the hair and for make-up applied to hairs and to the skin.

The colour of the hair, the skin and the facial and body hairs of human origin originates mainly from the melanin pigments secreted by the melanocytes.

These pigments of natural origin comprise, in particular, black or brown pigments which are referred to as eumelanins.

Their natural biosynthesis takes place in several stages by the polymerization of the oxidation products of an amino acid, namely tyrosine, and one of these oxidation products is 5,6-dihydroxyindole, which polymerizes in turn to eumelanin.

It is at present well known to dye human hair with 5,6-dihydroxyindole, making use either of metal salts, especially of transition metals, or of certain metal complexes of copper, cobalt, iron and manganese, in order to accelerate the process of oxidative polymerization of the indole derivative.

In make-up compositions for the skin, hairs, the eyelashes or the eyebrows, pigments based on metal compounds such as, for example, black and brown iron oxides, are used.

The safety of these compounds has, however, sometimes been called into question, so that those versed in the art were seeking pigments likely to present fewer problems in their cosmetic use.

The Applicant has just discovered that it was possible to prepare in vitro a non-allergenic, non-toxic natural pigment by employing at least one indole dye. This pigment is presented, more especially, in the form of ultrafine particles, dispersible in the cosmetically acceptable media customarily used for dyeing the hair, hairs or the skin.

The subject of the invention is hence an ultrafine powder containing melanin pigments.

Another subject of the invention consists in the preparation of this powder.

The invention also relates to the cosmetic application of such a powder, in particular in hair dyeing and in making-up the skin and hairs (eyelashes and eyebrows).

Other subjects of the invention will become apparent on reading the description and the examples which follow.

The powder according to the invention is essentially characterized in that it consists of inert inorganic particles having a particle size of less than 20 microns, and preferably less than 10 microns, and more especially less than or in the region of 5 microns, and containing on their surface a melanin pigment resulting from the oxidation of at least one indole dye of formula:

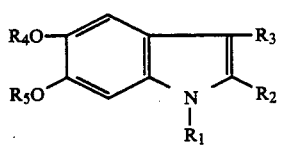
(I)

in which:
$R_1$ denotes a hydrogen atom, a lower alkyl group or a group —$SiR_9R_{10}R_{11}$;
$R_2$ and $R_3$, which may be identical or different, denote a hydrogen atom or alternatively a lower alkyl group, a carboxyl group, a lower alkoxycarbonyl group or a group —$COOSiR_9R_{10}R_{11}$; and
$R_4$ and $R_5$, which may be identical or different, denote a hydrogen atom, a linear or branched $C_1$–$C_{20}$ alkyl group, a formyl group, a linear or branched $C_2$–$C_{20}$ acyl group, a linear or branched $C_3$–$C_{20}$ alkenoyl group, a group —$SiR_9R_{10}R_{11}$, a group —$P(O)(OR_6)_2$ or a group $R_6OSO_2$, or alternatively $R_4$ and $R_5$, together with the oxygen atoms to which they are attached, form a ring optionally containing a carbonyl group, an optionally substituted methylene group, a thiocarbonyl group or a group:

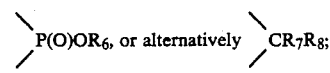

$R_6$ and $R_7$ denoting a hydrogen atom or a lower alkyl group, $R_8$ denoting a lower alkoxy group or a mono- or dialkylamino group, $R_9$, $R_{10}$ and $R_{11}$, which may be identical or different, denoting linear or branched lower alkyl groups, and the addition salts with inorganic or organic acids as well as the corresponding salts of alkali metals, alkaline earth metals or amines.

The particle size of these particles is generally greater than 0.01 micron.

The pigment thereby formed is the melanin pigment in the case of 5,6-dihydroxyindole.

By analogy, and for the sake of simplification, the pigment formed by oxidation of each of the compounds of the formula (I) will also be referred to as a "melanin" pigment.

The particles which are more especially usable can be particles of calcium carbonate or of silica having the particle size defined above.

Preferred indole dyes of the formula (I) correspond to the formula:

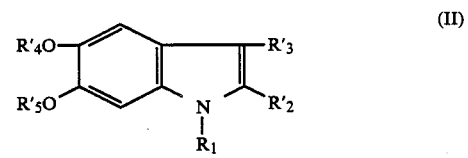
(II)

in which $R'_2$ and $R'_3$, which may be identical or different, denote a hydrogen atom, a $C_1$–$C_6$ lower alkyl group, a carboxyl group or a lower alkoxycarbonyl group in which the alkoxy group is a $C_1$–$C_6$ group, and $R'_4$ and $R'_5$, which may be identical or different, denote a hydrogen atom, a $C_1$–$C_6$ lower alkyl group, a $C_2$–$C_{20}$ linear acyl group or a trimethylsilyl group, or alternatively $R'_4$ and $R'_5$, together with the oxygen atoms to which they are attached, form an optionally substituted methylenedioxy or a carbonyldioxy ring.

The dyes which are more especially usable are chosen from 5,6-dihydroxyindole, 5-methoxy-6-hydroxyindole, 3-methyl,5,6-dihydroxyindole, 2-methyl-5,6-hydroxyindole, 5,6-bis(trimethylsilyoxy)indole, 5,6-[(1-ethoxyethyl)-1,1-dioxy]indole, 5,6-(methylenedioxy)indole, 5-acetoxy-6-hydroxyindole, 2-ethoxycarbonyl- 5,6-dihydroxyindole, 5-hydroxy-6-methoxyindole, 5,6-(carbonyldioxy)indole, 2-carboxy-5,6-dihydroxyindole, 2,3-dimethyl-5,6-dihydroxyindole and their salts.

The especially preferred embodiment employs 5,6-dihydroxyindole.

The process for preparing the powder according to the invention consists essentially in mixing in the air, with stirring, at room temperature, the indole dye of formula (I) and the inorganic inert particulate filler having the particle size defined above.

The formation of the "melanin pigment" is accomplished, in an aqueous medium, either in the air, preferably at alkaline pH, or by adding an oxidizing agent such as peroxides, and especially hydrogen peroxide, periodic acid and its water-soluble salts, potassium permanganate and dichromate, sodium hypochlorite, potassium ferricyanide, ammonium persulphate, silver oxide, ferric chloride, lead (Pb IV) oxide and caesium (Ce IV) sulphate, or by adding an alkali metal iodide, alkaline earth metal iodide or ammonium iodide and hydrogen peroxide.

The prefered water-soluble periodate is that of sodium.

The melanin pigment forms slowly in the air, the use of an alkaline pH activating the reaction.

When an oxidizing agent is used, the pH is immaterial, but it is preferably alkaline, in the case of the iodide/$H_2O_2$ system thereby enabling the reaction to be activated.

The especially preferred process consists in using an alkali metal iodide, alkaline earth metal iodide or ammonium iodide and hydrogen peroxide at an acidic or alkaline pH.

In this process, the indole dye of formula (I) is preferably used in proportions by weight of between 0.1 and 10%, and preferably between 0.5 and 5%, the particulate inert inorganic filler representing 0.05 to 10% by weight, and preferably 0.1 to 6% by weight. The remainder of the preparation generally consists of an aqueous medium.

The aqueous medium can optionally contain solvents, in proportions sufficient for rapidly solubilizing the indole dye of the formula (I). As a solvent which is especially usable, ethyl alcohol may be mentioned.

When iodide ions are used for forming the melanin pigment, they are preferably used in proportions of 0.07 to 4%, and preferably 0.7 to 3%, relative to the total weight of the composition, observing an indole dye/$I^-$ ratio of between 0.6 and 5, and more especially in the region of 3 to 4.

The pigment thus prepared may be added to traditional cosmetic vehicles at a concentration of between 1 and 35%, and preferably 2 to 20%, of the total weight of the composition, to produce hair dyeing compositions or make-up products, in particular for the eyelashes, the eyebrows or the skin, such as eye-shadows, blushers, eye-liners, and mascaras for the eyelashes and eyebrows. These cosmetic vehicles are known per se.

These compositions can be presented in the form of a lotion, thickened lotion, gel, cream, powder or stick, and can optionally be packaged as an aerosol.

The compositions used for making-up the skin, the eyelashes and the eyebrows can, in particular, be presented in solid or pasty, anhydrous or aqueous form, and in the latter case they comprise oil-in-water or water-in-oil emulsions or alternatively suspensions.

The compositions according to the invention have the advantage of being stable and rapidly prepared at room temperature, and are endowed with good safety properties.

When they are used in the form of emulsions, they can contain, in addition, surfactants which are well known in the prior art, chosen from anionic, nonionic, cationic or amphoteric surfactants.

The make-up compositions can contain, in particular, fats, organic solvents, silicones, thickeners, demulcents, antisun products, perfumes, preservatives, antioxidants, fillers, sequestering agents, anionic, cationic, nonionic and amphoteric polymers, as well as mixtures thereof, and alkalinizing or acidifying agents.

The fat can consist of an oil or a wax or a mixture thereof.

The oils are preferably chosen from animal, vegetable, mineral or synthetic oils, and, in particular, hydrogenated palm oil, hydrogenated castor oil, liquid paraffin, paraffin oil and purcellin oil.

The waxes are chosen from animal, fossil, vegetable, mineral or synthetic waxes, among which beeswax, carnauba, candelilla, sugar cane and Japan waxes, ozokerites, montan wax, microcrystalline waxes and paraffin waxes may be mentioned.

The compositions can also contain, in addition to the ultrafine particles containing the melanin pigments, other pigments generally used in cosmetics, in particular nacreous pigments that permit further variation in the colourings capable of being obtained.

The invention also relates to the hair dyeing and make-up process employing a powder as defined below.

The examples which follow are designed to illustrate the invention, no limitation of the latter being implied.

EXAMPLES 1, 2, 3, 4 AND 5

4g of 5,6-dihydroxyindole are dissolved in 10 g of ethyl alcohol in a beaker and with magnetic stirring. The following are then added successively at room temperature: water in a quantity necessary for obtaining 100 g of mixture in total, 20 g of "20 volumes" hydrogen peroxide, variable quantities of calcium carbonate (SOLVAY socal N)*, recorded in Table A below, and then, finally, 1.5 g of potassium iodide.

A black precipitate rapidly appears. The reaction is left to proceed to completion for 1 hour. The insoluble black pigment is separated off by filtration. It is washed with water. The precipitate is taken up with alcohol, filtered again and left to dry in the air. A black melanin pigment is obtained, the average particle size of which is shown in Table A below.

| EXAMPLE NO. | $CaCO_3$ (in g) | PARTICLE DIAMETER (in microns) |
| --- | --- | --- |
| 1 | 4.0 | 5 |
| 2 | 2.0 | 5 |
| 3 | 0.8 | 5 |
| 4 | 0.4 | 5 |
| 5 | 0.2 | 5 |

*average size < 3μ.

EXAMPLE 6

The following are added successively in a beaker; 1.6 g of micronized silica (SYLOBLOC 46, sold by the company GRACE), 1.6 g of 5,6-dihydroxyindole, 16 g of ethyl alcohol and 64 g of water.

The composition obtained is mixed at room temperature with magnetic stirring. 0.8 g of potassium iodide and, lastly, 16 g of "20 volumes" hydrogen peroxide are then introduced.

The black precipitate formed is then separated off in accordance with the method described in Examples 1 to 5.

The melanin pigment has a particle size of the order of 5μ.

EXAMPLE 7

The following are added successively in a beaker with magnetic stirring: 1.8 g of pyrogenic silica (AEROSIL 300, sold by the company DEGUSSA), 0.9 g of 5,6-dihydroxyindole, 0.5 g of ammonium iodide, 1.8 of ethyl alcohol, 84.2 g of water and then 10.8 g of "20 volumes" hydrogen peroxide.

The black precipitate formed is separated off in accordance with the method described in the Examples above.

The melanin pigment has a particle size of the order of 3μ.

EXAMPLE 8

The following are added successively in a beaker with magnetic stirring: 2.0 g of pyrogenic silica (AEROSIL R 972, sold by the company DEGUSSA), 1.0 g of ammonium iodide, 1.0 g of 5,6-dihydroxyindole, 29 g of ethyl alcohol, 46 g of water and then 21 g of "20 volumes" hydrogen peroxide.

The black precipitate formed is separated off in accordance with the method described in the Examples above.

The melanin pigment has a particle size of the order of 3μ.

EXAMPLE 9

The following are added successively in a beaker with magnetic stirring: 2.8 g of pyrogenic silica (AEROSIL 200, sold by the company DEGUSSA), 1.8 g of sodium iodide, 0.9 g of 5,6-dihydroxyindole, 6.5 g of ethyl alcohol, 79 g of water and then, lastly, 9 g of "20 volumes" hydrogen peroxide.

The black precipitate formed is separated off in accordance with the method described in the Examples above.

The melanin pigment has a particle size of the order of 3μ.

EXAMPLE 10

The following are added successively in a beaker: 0.58 g of 5,6-dihydroxyindole, 23.3 g of ethyl alcohol, 45.9 g of water and then 6.97 g of calcium carbonate (SOCAL N, sold by SOLVAY) while stirring magnetically.

After the addition of 0.58 g AS of Na periodate (equivalent to 23.25 g of aqueous periodate solution containing 2.5% AS), the reaction is left to proceed to completion for a few minutes.

After filtration and washing with water and then with ethyl alcohol, a black melanin pigment is obtained.

EXAMPLE 11

The following are added successively in a beaker with magnetic stirring:
2.77 g of 2-methyl-5,6-dihydroxyindole hydrobromide;
13.9 g of ethyl alcohol;
66.7 g of water, and then
9.25 g of "20 volumes" aqueous hydrogen peroxide solution;
4.60 g of pyrogenic silica (AEROSIL 200, sold by DEGUSSA) and, lastly,
2.78 g of potassium iodide.

After a few minutes for the reaction to proceed to completion, followed by filtration and washing with water and ethyl alcohol, a bluish-black melanin pigment is obtained.

EXAMPLE 12

The following are added successively in a beaker with magnetic stirring:
4.45 g of 2,3-dimethyl-5,6-dihydroxyindole hydrobromide;
40 g of ethyl alcohol;
38.9 g of water, and then
11.1 g of "20 volumes" aqueous hydrogen peroxide solution;
2.78 g of pyrogenic silica (AEROSIL 200, sold by DEGUSSA) and, lastly,
2.78 g of potassium iodide.

After filtration and washing with water and then with ethyl alcohol, a black melanin pigment having an auburn glint is obtained.

EXAMPLE 13

The following are added successively in a beaker with magnetic stirring:
4.4 g of 5-methoxy-6-hydroxyindole;
36.3 g of ethyl alcohol;
36.3 g of water, and then
1.4 g of potassium iodide;
3.6 g of calcium carbonate (SOCAL N, sold by SOLVAY) and, lastly,
18 g of "20 volumes" aqueous hydrogen peroxide solution.

After filtration and washing with water and then with ethyl alcohol, a black melanin pigment having grey glints is obtained.

EXAMPLE 14

The following are added successively in a beaker with magnetic stirring:
4.4 g of 5-acetoxy-6-hydroxyindole;
29.4 g of ethyl alcohol;
29.4 g of water, and then
5.9 g of calcium carbonate (SOCAL N, sold by SOLVAY);
1.5 g of potassium iodide and, lastly,
29.4 g of "20 volumes" aqueous hydrogen peroxide solution.

After filtration and washing with water and then with ethyl alcohol, a pinkish light beige melanin pigment is obtained.

EXAMPLE 15

The following are added successively in a beaker with magnetic stirring:
1.83 g of 3-methyl-5,6-dihydroxyindole;
26.2 g of ethyl alcohol;
37.4 g of water;
0.52 g of potassium iodide, and then
7.85 g of calcium carbonate (SOCAL N, sold by SOLVAY) and, lastly,
26.2 g of "20 volumes" aqueous hydrogen peroxide solution.

After filtration and washing with water and then with ethyl alcohol, a midnight blue melanin pigment is obtained.

EXAMPLE 16

The following are added successively in a beaker with magnetic stirring:
2.4 g of 5-methoxy-6-hydroxyindole;
26.6 g of ethyl alcohol;
40 g of water;
4.3 g of calcium carbonate (SOCAL N, sold by SOLVAY) and then, lastly,
26.7 g of a 15% strength aqueous sodium periodate solution (equivalent to 4 g AS).

After filtration and washing with water and with ethyl alcohol, a black melanin pigment is obtained.

EXAMPLE 17

The following are added successively in a beaker with magnetic stirring:
0.6 g of 2-carboxy-5,6-dihydroxyindole;
29.8 g of ethyl alcohol;
29.3 g of water, and then
4.5 g of calcium carbonate (SOCAL N, sold by SOLVAY) and, lastly,
12 g of ammonium persulphate in 10% strength aqueous solution, equivalent to 1.2 g AS.

After filtration and washing with water and ethyl alcohol, a black melanin pigment is obtained.

EXAMPLE 18

The following are added successively in a beaker with magnetic stirring:
0.5 g of 5,6-dihydroxyindole;
42.1 g of ethyl alcohol;
10 g of water, and then
5.3 g of calcium carbonate (SOCAL N, sold by SOLVAY) and, lastly,
42.1 g of a 1.5% strength aqueous potassium permanganate solution, equivalent to 0.63 g AS.

After filtration and washing with water and then with ethyl alcohol, a medium grey melanin pigment is obtained.

EXAMPLE 19

The following are added successively in a beaker with magnetic stirring:
0.7 g of 5,6-[(1-ethoxyethyl)-1,1-dioxy]indole;
46.3 g of ethyl alcohol;
14.7 g of water, and then
4.3 g of calcium carbonate (SOLVAY SOCAL N), and, lastly, 34 g of a 10% strength aqueous potassium dichromate solution, equivalent to 3.4 g AS.

After filtration, and washing with water and then with alcohol, a light brown melanin pigment is obtained.

EXAMPLE 20

The following are added successively in a beaker with magnetic stirring:
0.3 g of 5,6-(carbonyldioxy)indole;
25 g of ethyl alcohol;
34.7 g of water, and then
4 g of calcium carbonate (SOCAL N, sold by SOLVAY) and, lastly,
20 g of a 10% strength aqueous ammonium persulphate solution, equivalent to 2 g AS.

After filtration and washing with water and with ethyl alcohol, a medium grey melanin pigment is obtained.

EXAMPLE 21

2 g of powder obtained according to Example 5 are introduced into 90 g of a gel of the following composition:

| | |
|---|---|
| Celquat L 200 | 1.0 g |
| Methacrylic acid/methyl methacrylate 50/50 copolymer | 1.0 g |
| Ethyl alcohol, 96° strength | 8.5 g |
| Perfume, preservative qs | |
| Water qs | 100 g |

The gel thereby obtained is applied on hair that is 90% white, and the composition is left in place for 15 to 20 minutes. The hair is rinsed with water.

After drying, the hair is dyed dark grey, almost black.

The powder obtained in Example 5 can be replaced in this example by that of Example 10.

EXAMPLE 22

An oil-in-water emulsion having the following composition is prepared:

| | |
|---|---|
| Stearic acid | 10.0 g |
| Candelilla wax (M.p 66/71° C.) | 3.0 g |
| Beeswax (M.p. 61/65° C.) | 5.0 g |
| Microcrystalline wax (M.p. 89° C.) | 10.0 g |
| Triethanolamine | 3.0 g |
| Guar gum | 3.0 g |
| Methylcellulose | 0.2 g |
| Methyl para-hydroxybenzoate | 0.1 g |
| Propyl para-hydroxybenzoate | 0.1 g |
| Pigment based on 5,6-dihydroxyindole on calcium carbonate, 50:50 | 20.0 g |
| Hydroxyethylcellulose | 2.0 g |
| Sterile deionized water qs | 100.0 g |

This composition is used as an automatic mascara.

The pigment in this example can be replaced by that obtained in Example 15.

EXAMPLE 23

An oil-in-water emulsion having the following composition is prepared:

| | |
|---|---|
| Stearic acid | 1.0 g |
| Carnauba wax (M.p. 83/86° C.) | 1.0 g |
| Hydrogenated castor oil | 3.0 g |
| Triethanolamine | 0.4 g |
| Methylhydroxypropylcellulose | 2.5 g |
| Polyethylene glycol 1,500 | 12.0 g |
| Methyl para-hydroxybenzoate | 0.1 g |
| Propyl para-hydroxybenzoate | 0.1 g |
| Ethyl para-hydroxybenzoate | 0.1 g |
| Magnesium silicate | 0.5 g |
| Pigment based on 5,6-dihydroxyindole on calcium carbonate, 50:50 | 17.0 g |
| Sterile deionized water qs | 100.0 g |

This composition is used for accentuating the rims of the eye, and is commonly designated an "eye-liner".

The above pigment can be replaced by that obtained in Example 16.

EXAMPLE 24

The following emulsion is prepared:

| | |
|---|---|
| Stearic acid | 3.0 g |
| Microcrystalline wax | 1.0 g |

| | |
|---|---|
| -continued | |
| Hydrogenated palm oil | 2.0 g |
| Triethanolamine | 1.2 g |
| Polyethylene glycol 1,500 | 15.0 g |
| Magnesium silicate | 0.6 g |
| Propyl para-hydroxybenzoate | 0.1 g |
| Methyl para-hydroxybenzoate | 0.1 g |
| Imidazolidinylurea | 0.3 g |
| Titanium dioxide | 3.0 g |
| Titanium dioxide-coated mica | 15.0 g |
| Pigment based on 5,6-dihydroxyindole on calcium carbonate, 50:50 | 4.0 g |
| Darvan 7 (sodium polymethacrylate) | 0.5 g |
| Sterile deionized water qs | 100.0 g |

This composition is used as an eye-shadow.

The pigment can be replaced by that described in Example 19 or 20.

I claim:

1. A powder consisting of inert inorganic particles having a particle size ranging from 0.01 to 20 microns, said particles containing on their surface a melanin pigment resulting from the oxidation of at least one indole dye having the formula

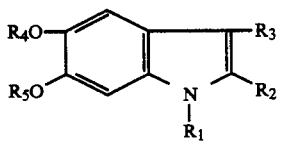
(I)

wherein $R_1$ represents hydrogen, alkyl having 1-6 carbon atoms or $-SiR_9R_{10}R_{11}$, $R_2$ and $R_3$, each independently, represent hydrogen, alkyl having 1-6 carbon atoms, carboxyl, alkoxy carbonyl wherein the alkoxy moiety has 1-6 carbon atoms or $-COOSiR_9R_{10}R_{11}$, $R_4$ and $R_5$, each independently, represent hydrogen, linear or branched $C_1-C_{20}$ alkyl, formyl, linear or branched $C_2-C_{20}$ acyl, linear or branched $C_3-C_{20}$ alkenyl, $-SiR_9R_{10}R_{11}$, $-P(O)(OR_6)_2$ or $R_6OSO_2$, or $R_4$ and $R_5$, together with the oxygen atoms to which they are attached, form a ring containing a carbonyl group, a methylene group, a thiocarbonyl group, a $>P(O)OR_6$ group or a $>CR_7R_8$ group, $R_6$ and $R_7$ represent hydrogen or alkyl having 1-6 carbon atoms, $R_8$ represents alkoxy having 1-6 carbon atoms or mono- or dialkyl amino, $R_9$, $R_{10}$ and $R_{11}$, each independently, represent linear or branched $C_1-C_6$ alkyl, and the addition salt thereof with an inorganic or organic acid, or the corresponding salt of an alkali metal, an alkaline earth metal or an amine.

2. The powder of claim 1 wherein said indole dye has the formula

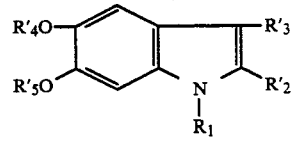
(II)

wherein $R'_2$ and $R'_3$, each independently, represent hydrogen, $C_1-C_6$ alkyl, carboxyl or alkoxycarbonyl wherein the alkoxy moiety has 1-6 carbon atoms, and $R'_4$ and $R'_5$, each independently, represent hydrogen, $C_1-C_6$ alkyl, linear $C_2-C_{20}$ acyl or trimethylsilyl, or $R'_4$ and $R'_5$, together with the oxygen atoms to which they are attached, form a methylenedioxy or carbonyldioxy ring.

3. The powder of claim 1 wherein said indole dye is selected from the group consisting of 5,6-dihydroxyindole,
5-methoxy-6-hydroxyindole,
3-methyl-5,6-dihydroxyindole,
2-methyl-5,6-dihydroxyindole,
5,6-bis(trimethylsiloxy)indole,
5,6-[(1-ethoxyethyl)-1,1-dioxy]indole,
5,6-(methylenedioxy) indole,
5-acetoxy-6-hydroxyindole,
2-ethoxycarbonyl-5,6-dihydroxyindole,
5-hydroxy-6-methoxyindole,
5,6-(carbonyldioxy) indole,
2-carboxy-5,6-dihydroxyindole,
2,3-dimethyl-5,6-dihydroxyindole, and the salts thereof.

4. The powder of claim 1 wherein said particles have a particle size less than 10 microns.

5. The powder of claim 1 wherein said particles have a particle size less than or about 5 microns.

6. The powder of claim 1 wherein said particles consist of calcium carbonate or silica.

7. A powder consisting of inert inorganic particles having a particle size ranging from 0.01 to 20 microns, said particles containing on their surface a melanin pigment resulting from the oxidation of 5,6-dihydroxyindole.

8. A cosmetic composition for dyeing hair or making up the skin, eyelashes or eyebrows comprising in a cosmetically acceptable medium in an amount effective to dye said hair or to make up said skin, eyelashes or eyebrows the powder of claim 1.

9. The cosmetic composition of claim 8 wherein said powder is present in an amount ranging from 1 to 35 percent by weight.

10. The cosmetic composition of claim 8 wherein said powder is present in an amount ranging from 2 to 20 weight percent.

11. The cosmetic composition of claim 8 which also contains at least one of an anionic, nonionic, cationic or amphopheric surfactant or a mixture thereof; a fat; a silicone; an organic solvent; a thickener; a demulcent; an anti-sun product; a perfume; a preservative; an antioxidant; a filler; a sequestering agent; an anionic, cationic, nonionic or amphoteric polymer or a mixture thereof; an alkalinizing agent and an acidifying agent.

* * * * *